United States Patent
Lee et al.

(10) Patent No.: US 8,583,224 B2
(45) Date of Patent: Nov. 12, 2013

(54) IMPLANTABLE MEDICAL DEVICE AND METHODS FOR AUTOMATED DETECTION OF INFECTION

(75) Inventors: Kent Lee, Shoreview, MN (US); Jonathan T. Kwok, Denville, NJ (US); Hugo Andres Belalcazar, Saint Paul, MN (US); Jennifer Lynn Pavlovic, Afton, MN (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 938 days.

(21) Appl. No.: 11/833,548

(22) Filed: Aug. 3, 2007

(65) Prior Publication Data
US 2008/0064980 A1  Mar. 13, 2008

Related U.S. Application Data

(60) Provisional application No. 60/825,101, filed on Sep. 8, 2006.

(51) Int. Cl.
*A61B 5/05* (2006.01)

(52) U.S. Cl.
USPC ........... 600/547; 600/300; 600/301; 600/481; 600/529; 607/3; 607/6; 607/18; 607/21; 607/22

(58) Field of Classification Search
USPC ........ 600/300–301, 547; 607/3, 6, 18, 21–22
See application file for complete search history.

(56) References Cited

U.S. PATENT DOCUMENTS

| | | | |
|---|---|---|---|
| 3,781,837 A * | 12/1973 | Anderson et al. | 600/549 |
| 4,160,205 A * | 7/1979 | Hobbs et al. | 324/692 |
| 5,957,861 A * | 9/1999 | Combs et al. | 600/547 |
| 6,282,444 B1 * | 8/2001 | Kroll et al. | 607/3 |
| 6,937,900 B1 | 8/2005 | Pianca et al. | |
| 6,963,772 B2 | 11/2005 | Bloom et al. | |
| 6,978,182 B2 | 12/2005 | Mazar et al. | |
| 7,052,488 B2 | 5/2006 | Uhland | |
| 7,130,679 B2 * | 10/2006 | Parsonnet et al. | 600/547 |
| 2003/0199783 A1 * | 10/2003 | Bloom et al. | 600/549 |
| 2004/0102712 A1 | 5/2004 | Belalcazar et al. | |
| 2004/0215097 A1 * | 10/2004 | Wang | 600/547 |
| 2005/0012610 A1 * | 1/2005 | Liao et al. | 340/539.12 |
| 2005/0043675 A1 * | 2/2005 | Pastore et al. | 604/67 |
| 2005/0070778 A1 * | 3/2005 | Lackey et al. | 600/366 |

(Continued)

OTHER PUBLICATIONS

U.S. Appl. No. 11/383,933, filed May 17, 2006.

(Continued)

*Primary Examiner* — Rene Towa
(74) *Attorney, Agent, or Firm* — Pauly, DeVries Smith & Deffner, L.L.C.

(57) ABSTRACT

The invention relates to systems, devices, and methods for detecting infections associated with implantable medical devices. In an embodiment, the invention includes a method of detecting infection in a patient including measuring a physiological parameter using a chronically implanted sensor at a plurality of time points and evaluating the physiological parameter measurements to determine if infection is indicated. In an embodiment, the invention includes an implantable medical device including a first chronically implantable sensor configured to generate a first signal corresponding to a physiological parameter and a controller disposed within a housing, the controller configured to evaluate the first physiological parameter signal to determine if an infection is indicated. Other embodiments are also included herein.

19 Claims, 12 Drawing Sheets

(56) References Cited

U.S. PATENT DOCUMENTS

| 2005/0131501 | A1* | 6/2005 | Rowland, III | 607/96 |
| 2006/0004431 | A1* | 1/2006 | Fuller et al. | 607/116 |
| 2006/0017575 | A1* | 1/2006 | McAdams | 340/573.1 |
| 2006/0052782 | A1* | 3/2006 | Morgan et al. | 606/60 |
| 2006/0127912 | A1* | 6/2006 | Pachot | 435/6 |
| 2006/0264776 | A1* | 11/2006 | Stahmann et al. | 600/547 |
| 2008/0262322 | A1* | 10/2008 | Gerber et al. | 600/301 |
| 2008/0262331 | A1* | 10/2008 | Gerber et al. | 600/361 |
| 2008/0262332 | A1* | 10/2008 | Gerber et al. | 600/361 |
| 2008/0262374 | A1* | 10/2008 | Gerber et al. | 600/547 |
| 2008/0262379 | A1* | 10/2008 | Gerber et al. | 600/549 |

OTHER PUBLICATIONS

Byrd, "Management of Implant Complications", Chap. 27 in Clinical Cardiac Pacing and Defibrillation $2^{nd}$ Ed., W.B. Saunders Company (2000).

Cabell, et al., "Increasing Rates of Cardiac Device Infections Among Medicare Beneficiaries: 1990-1999", *Am. Heart J.* (Apr. 2004), 147(4):582-586.

Chamis, et al., "S. Aureus Bacterium in Patients with Permanent PM or ICDs", *Circ.* (Aug. 28, 2001), 104:1029-1033.

Chua, et al., "Diagnosis and Management of Infections Involving Implantable EP Cardiac Devices", *Annals of Int. Med.* (Oct. 17, 2000), 133(8):604-608.

Kalashnik, A F. et al., "Impedometry in Prophylaxis and Early Diagnostics of Suppuration of Post-Operational Wounds", *Sov. Med.* (1981), 11:49-51 (translation attached).

Povoa, P. et al., "C-Reactive Protein as a Marker of Infection in Critically Ill Patients", *Clin. Microbiol. Infect.* (Feb. 2005), 11:101-108.

Voigt, et al., Rising Rates of Cardiac Rhythm Management Device Infections in the US: 1996 through 2003, (Aug. 1, 2006) *JACC* 48(3):590-591.

Biomaterials Science: An Introduction to Materials in Medicine p. 165-173 (Buddy D. Ratner et al. eds., 1996).

* cited by examiner ions associated with implantable medical devices.

IMPLANTABLE MEDICAL DEVICE AND METHODS FOR AUTOMATED DETECTION OF INFECTION

This application claims the benefit of U.S. Provisional Application No. 60/825,101, filed Sep. 8, 2006, the content of which is herein incorporated by reference.

FIELD OF THE INVENTION

The invention relates to implantable medical devices, and in particular, to systems, devices, and methods for detecting infections associated with implantable medical devices.

BACKGROUND OF THE INVENTION

Cardiac rhythm management (CRM) devices are implanted in patients to provide various forms of electrical stimulation therapy. The number of such devices implanted into patients is generally increasing as a larger number of people are indicated for the therapy. However, the implantation of a medical device carries a risk of infection. As such, the increased rate of implantation results in more patients being placed at risk for infection. Some studies have indicated that patients have a 2-10% risk of infection after implant. The risk of infection is typically higher on revision procedures (device re-vision, change out, etc.) compared to de novo implants. The incidence of infection generally has a bi-modal distribution, where infections are most likely to occur either immediately after implant or several months after implant.

Infections carry a significant risk to the patient. Most infections begin at the pocket area where the device is implanted. If such infections spread to the stimulation leads and into the heart, complete CRM system explant and re-implant of a new device is usually required. Considerable risks are associated with explant, particularly lead extraction. In addition, these infections come at a tremendous cost to the healthcare system. Explant of a CRM system is very expensive and can include medical stays lasting several days until the infection has been cleared and a new device can be re-implanted.

It is difficult for clinicians caring for patients with implanted pacemakers or ICDs to detect infections. It is particularly difficult to detect infections at an early stage when non-surgical therapeutic intervention, such as the administration of anti-microbial active agents, would be most effective. For at least these reasons, a need exists for devices capable of detecting infections and related methods.

SUMMARY OF THE INVENTION

Amongst other embodiments, this invention discloses the use of sensors to monitor for signs of infection, where often these signs of infection are sub-clinical, allowing early intervention, and possibly preventing the need for system explant and subsequently preventing complications.

In an embodiment, the invention includes a method of detecting infection in a patient including measuring a physiological parameter using a chronically implanted sensor at a plurality of time points and evaluating the physiological parameter measurements to determine if infection is indicated.

In an embodiment, the invention includes an implantable medical device including a first chronically implantable sensor configured to generate a first signal corresponding to a physiological parameter and a controller disposed within a housing, the controller configured to evaluate the first physiological parameter signal to determine if an infection is indicated.

The invention may be more completely understood by considering the detailed description of various embodiments of the invention that follows in connection with the accompanying drawings.

Figure 1:
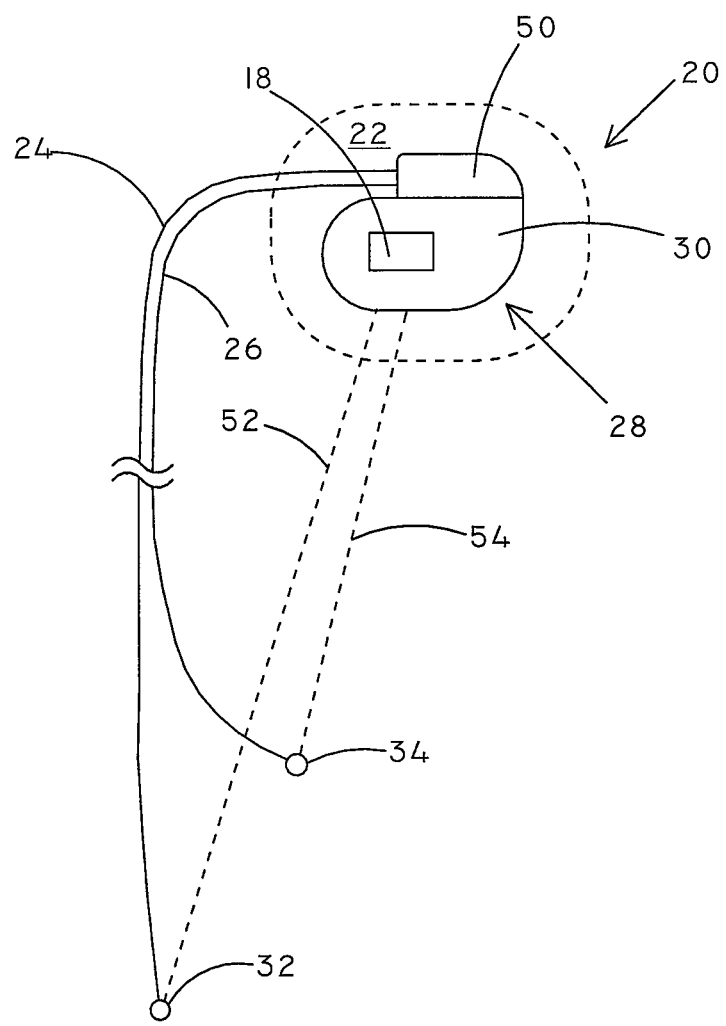
FIG. 1 is a schematic view of an implantable device in accordance with an embodiment of the invention.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

Many different types of medical devices are implanted in patients to provide medical therapy or treatment. One type of implantable medical device is a cardiac rhythm management device (CRM). There are various types of CRM devices including pacemakers, implantable cardioverter defibrillators (ICDs), cardiac resynchronization therapy (CRT) devices, and the like. Infections are a serious problem associated with the implantation of medical devices. Some studies have indicated that patients have a 2-10% risk of infection after implantation of a CRM device.

Embodiments of the present invention can include implantable medical devices and systems, such as CRM devices, configured to detect the presence of an infection in a patient. Infections lead to a physiological response that can include swelling, fluid discharge, and increased temperature, amongst other effects. Embodiments of systems and devices included herein can include sensors configured to measure properties that are modulated by infections in order to detect the onset of infection. In some embodiments, devices included herein can detect infections prior to the onset of clinical symptoms, allowing the physician to intervene to prevent the infection from worsening and spreading.

In the case of implanted device infections, it is nearly always the case that such infections are first seen in the pocket where the device is located. In some embodiments, systems and devices of the invention are capable of detecting an infection in the tissue pocket in which the device is implanted. Sensors associated with systems and devices described herein can measure physiological properties associated with the fluid environment of the pocket to detect the onset of pocket infection.

However, it will be appreciated that systems and devices of the invention can also be used to detect infections in other areas of a patient's body beyond the tissue pocket into which the medical device is implanted. In some embodiments, systems and devices of the invention can include sensors disposed outside of the pocket area. Data from these sensors can be analyzed in order to detect signs of infection. It is believed that symptoms of some infections can become generalized to the extent that physiological changes due to infections occurring elsewhere in the body are also reflected in the pocket where the device is located. As such, in some embodiments, sensors disposed within the pocket area can also be used in order to detect signs of an infection occurring outside of the pocket area.

A first embodiment of a system constructed according to the principles of the invention is depicted in FIG. 1. A device 20, such as a CRM device, is implanted within a tissue pocket 22 of a patient. Device 20 typically includes a pulse generator 28, including a housing 30 and a header 50. The device 20 can also include a first stimulation lead 24 and a second stimulation lead 26. Housing 30 is configured to contain the electronic circuitry of the device 20, and typically is formed from a metal such as titanium. Device 20 further includes a controller 18. Controller 18 can include electronic circuitry for receiving and processing signals, such as signals from sensors and from the stimulation leads 24, 26, as well as circuitry for communicating with a device outside of the patient's body. For example, the controller 18 can be configured to communicate wirelessly with a programmer that is located near the patient. The controller 18 can also include circuitry that is configured to generate electrical stimulation pulses.

First stimulation lead 24 and second stimulation lead 26 extend from pulse generator 28 to a target tissue, such as cardiac tissue. First stimulation lead 24 and second stimulation lead 26 are each configured to transmit and/or receive an electrical signal from pulse generator 28 to a region of a heart that is capable of affecting pacing of the heart or that conducts a signal representative of the operation of the heart. First and second stimulation leads 24, 26, each have an electrode 32, 34, respectively, that is configured to engage a target tissue and to transmit an electrical signal to the target tissue, such as the right or left atrium or ventricle. In some embodiments, the stimulation leads can be bipolar and can include two electrodes each. In some embodiments, the device may only include one stimulation lead.

In the embodiment of FIG. 1, the device 20 is configured to measure impedance in the body tissue proximal to housing 30. Measuring impedance of the tissue in or near the pocket 22 can provide an indication of the presence of an infection in pocket 22. In one embodiment, measuring impedance comprises receiving a signal at controller 18 that corresponds to the impedance value.

Figure 2:
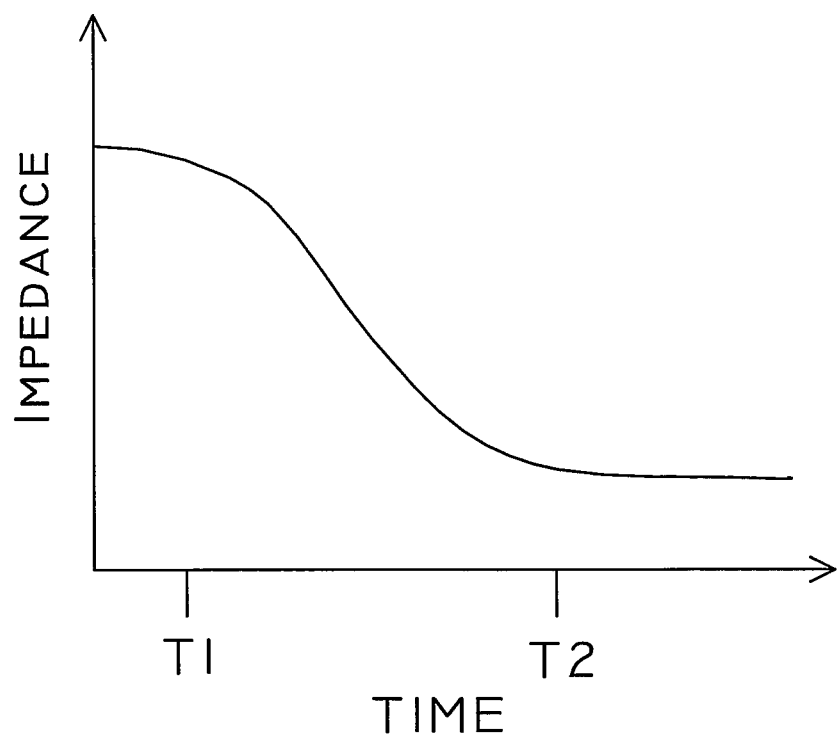
FIG. 2 is a chart showing an impedance signal over time indicating the presence of an infection.

Many techniques for measuring impedance proximal to an implantable device can be used. For example, one usable technique is described in Published U.S. Patent Application 2004/0102712, which is incorporated herein by reference in its entirety. Generally, a current is provided from electrode 32 that travels through the body tissue to housing 30 (represented by path 52). Simultaneously, the voltage differential between housing 30 and electrode 34 is monitored (represented by path 54). Based on the relationship between current and voltage, the impedance of the body tissue can be determined. Alternatively, the current drive and voltage sense vectors (paths) can be switched.

Where the pocket 22 is infected, various changes occur to the tissue including the formation of pus or clear fluids. Accumulation of these fluids tend to result in reduced impedance in comparison to non-infected tissue. Therefore, tracking impedance over time can provide an indication of the presence of an infection if the impedance declines. While not intending to be bound by theory, it is believed that this can allow detection of an infection before clinical symptoms exist. Referring now to FIG. 2, a hypothetical chart of average impedance over time during the course of an infection is shown. At a first time T1, impedance is relatively high when there is no infection. However, as time passes impedance is shown as decreasing as a result of an infection. By time T2, impedance has decreased significantly as a result of the infection. As such, it is believed that the detection of decreasing impedance can allow a diagnosis of infection before clinical symptoms appear.

It will be appreciated that impedance can be affected by factors other than the onset of an infection. By way of example, impedance can vary based on posture, activity, fluid distribution, etc. As such, in some embodiments, an impedance signal can be processed in order to derive changes that may be occurring specifically as a result of an infection. By way of example, in some embodiments, impedance values can be averaged over some time interval to smooth out daily variation in impedance. It will be appreciated that there are many other techniques of reducing or eliminating variations in the impedance signal that are due to factors other than the onset of an infection.

In some embodiments, the system can include a posture sensor in order to account for changes to the impedance measurements that may be caused by changes in the patient's posture. For example, a posture sensor can include a three-axis accelerometer that is capable of sensing the orientation of the patient's body with respect to the earth's gravitational field. An exemplary accelerometer is described in U.S. Pat. No. 6,937,900, the contents of which are herein incorporated by reference. A posture sensor can detect whether the patient is generally horizontal or generally vertical, or somewhere in between. In some embodiments, an impedance measurement is only taken or only used when the patient's posture satisfies a predefined criterion, such as the patient being generally horizontal. In some other embodiments, the impedance measurements are corrected or adjusted based on the signal from the posture sensor.

Figure 3:
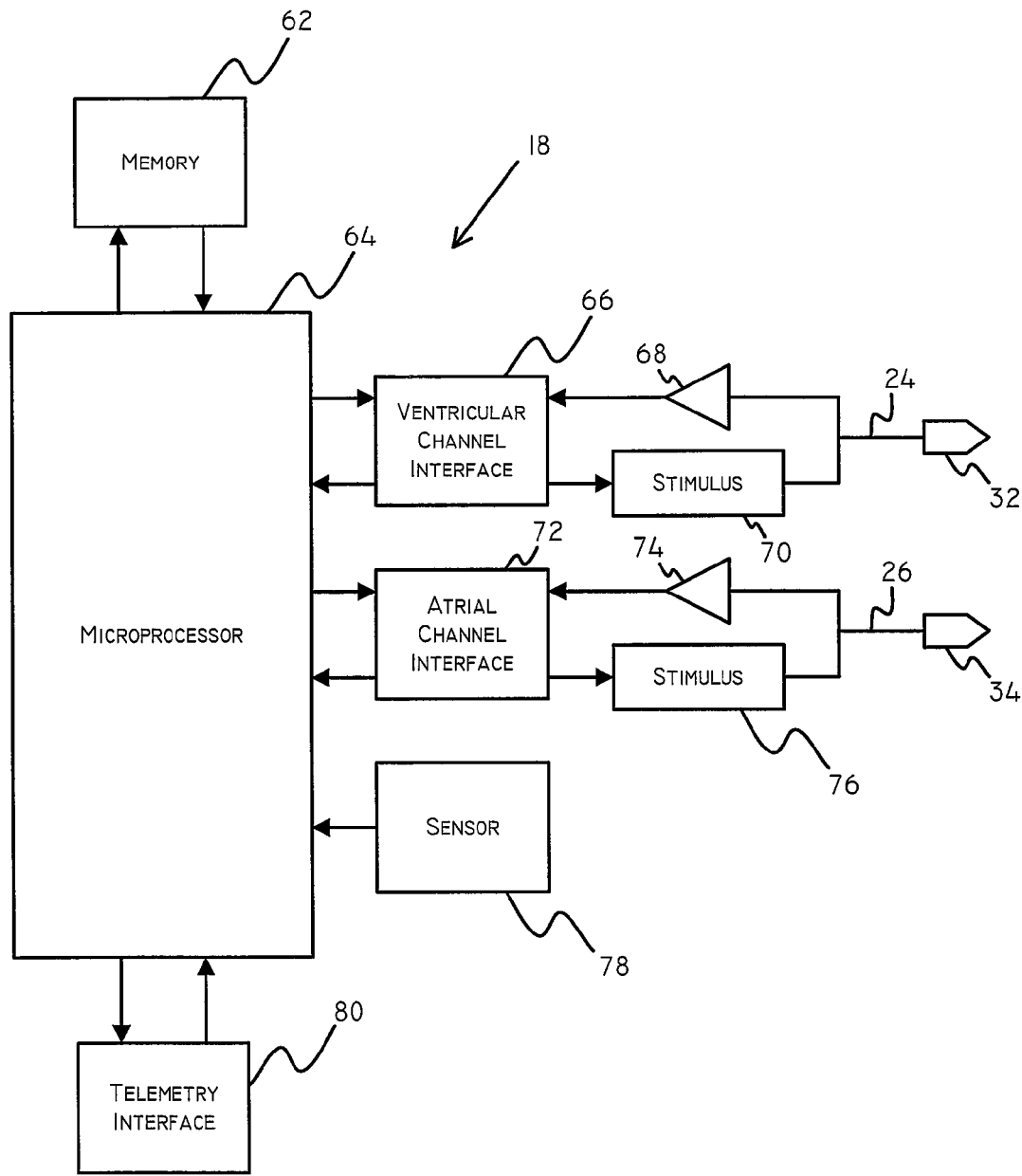
FIG. 3 is a schematic view of some components of a controller in accordance with an embodiment of the invention.

It will be appreciated that the controller 18 can include various electronic components and can be configured to perform operations and methods as described herein. Referring now to FIG. 3, a schematic diagram is shown of some components of an exemplary controller 18. The controller 18 can include a microprocessor 64. Microprocessor 64 can execute instructions and can communicate with memory 62 via a bi-directional data bus. The memory 62 typically comprises ROM (read only memory) for program storage and/or RAM (random access memory) for data storage. The controller can include atrial sensing and pacing channels comprising sensing amplifier 74, output circuit 76, and an atrial channel interface 72, in communication with electrode 34 and stimulation lead 26. The controller can also include ventricular sensing and pacing channels comprising sensing amplifier 68, output circuit 70, and ventricular channel interface 66, in communication with electrode 32 and stimulation lead 24. Each channel can communicate bi-directionally with a port of microprocessor 64. For each channel, the same stimulation lead and electrode can be used for both sensing and pacing. The channel interfaces 66 and 72 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. The controller 18 can also interface with one or more sensors 78, such as an accelerometer, a posture sensor, an impedance sensor, a minute ventilation sensor, a pressure sensor, a temperature sensor, or the like. The controller 18 can also interface with a telemetry module 80 for communicating with an external programmer or a patient management system. An exemplary patient management system includes the LATITUDE® patient management system, commercially available from Boston Scientific Corporation, Natick, Mass. Aspects of an exemplary patient management system are described in U.S. Pat. No. 6,978,182, the content of which is herein incorporated by reference. In some embodiments, data gathered with the implantable device can be displayed on the external programmer and/or the patient management system. For example, an impedance trend can be displayed on the external programmer and/or the patient management system.

Figure 4:
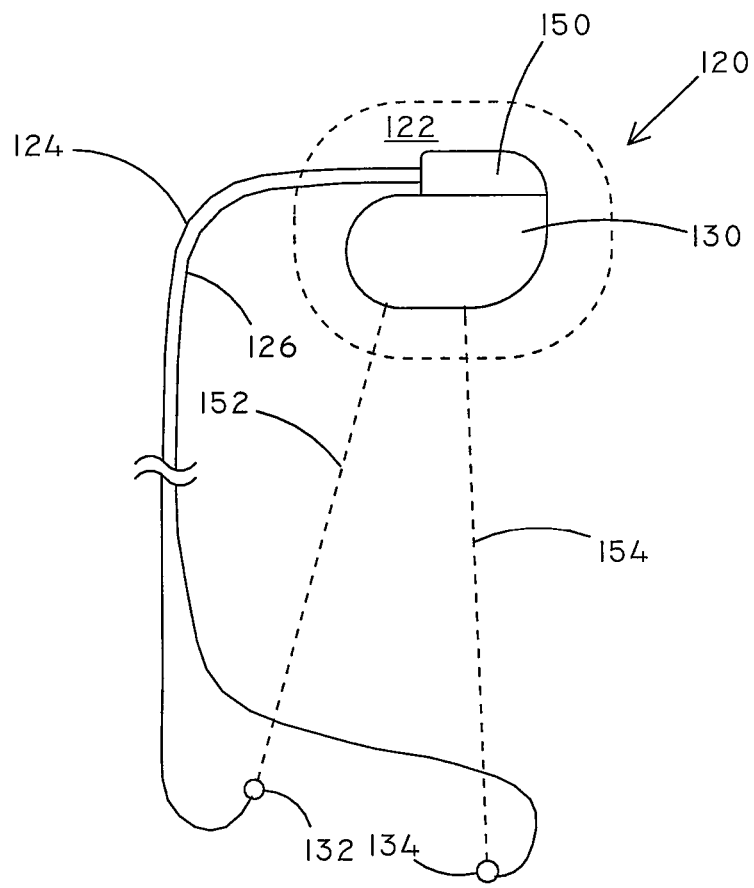
FIG. 4 is a schematic view of an alternative embodiment of an implantable device in accordance with an embodiment of the invention.

When measuring impedance through body tissue, it is desirable for the measurement vectors to be as orthogonal as possible to each other. It is believed that this causes the assessment of impedance to more accurately reflect conditions near the intersection of the measurement vectors, in this case the area around the housing. Referring now to FIG. 4, a schematic view is shown of a device with an alternative arrangement of stimulation leads and electrodes providing measurement vectors that are more orthogonal than that depicted in FIG. 1. The device 120 includes housing 130 and header 150. The device 120 also includes a first stimulation lead 124 and a second stimulation lead 126. A first electrode 132 is disposed on the distal end of first stimulation lead 124 and a second electrode 134 is disposed on the distal end of second stimulation lead 126. In this embodiment, for example, a current can be generated between electrode 132 and housing 130 (represented by path 152). Voltage can be measured between electrode 134 and housing 130 (represented by path 154). Then impedance can be calculated based on the known current and the measured voltage. Paths 152 and 154 are more orthogonal to one another than are paths 52 and 54 shown in FIG. 1. As such, it is believed that the configuration shown in FIG. 4 can be used to generate an impedance signal that is more reflective of impedance in pocket 122.

Figure 5:
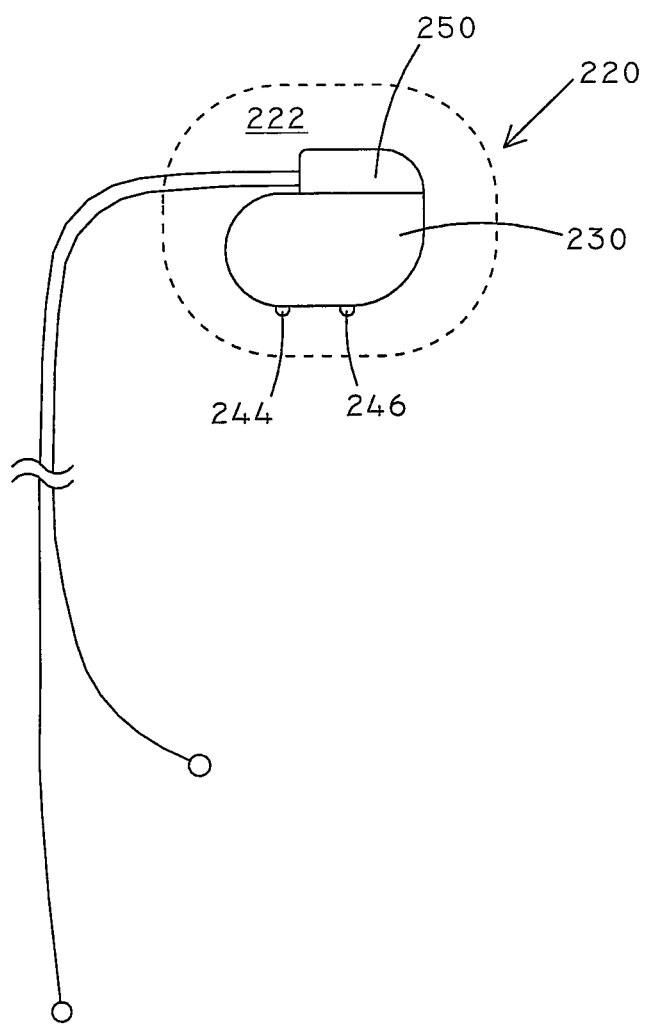
FIG. 5 is a schematic view of an alternative embodiment of an implantable device in accordance with an embodiment of the invention.

A further embodiment of a system for detecting infection is depicted in FIG. 5. This embodiment includes a pair of electrodes 244, 246 disposed within the tissue pocket 222 holding the device 220. In this embodiment, the electrodes 244, 246 are disposed on the device housing 230. However, it will be appreciated that one or both of the electrodes can also be disposed on the device header 250. Impedance can be measured by the system of FIG. 5 in a similar manner to that described with respect to the systems of FIGS. 1 and 4, except that a current can be generated between electrode 244 and the device 220 housing, and a voltage measured between electrode 246 and the device 220 housing, then an impedance can be calculated from the known current and measured voltage. This has the advantage that it is measuring primarily or exclusively the impedance of the tissue immediately surrounding the implantable device 220. As shown in FIG. 2, a decrease in the impedance measurement can be indicative of the onset of infection.

It will be appreciated that the onset of infection can be detected through techniques other than measuring impedance. Infections can create other detectable changes including temperature changes, changes in the concentrations of various analytes, pressure changes, and the like. As such, some embodiments of the system can include sensors to detect properties other than impedance. Table 1 below illustrates some physiological parameters that can change in response to an infection along with the trend or state that would be expected to indicate infection. Embodiments of the invention can be configured to detect changes in one or more of the physiological parameters of Table 1 in order to detect the presence of an infection.

TABLE 1

| Physiological Parameter | Trend/State Indicating Infection |
| --- | --- |
| Impedance | Decreasing Impedance |
| Temperature | Increasing Temperature |
| Pressure | Increasing Pressure |
| Lactate | Increasing Concentration of Lactate |
| pH | Decreasing pH |
| C-reactive protein (CRP) | Increasing Concentration of CRP |
| Lipopolysaccharide (LPS) | Detection of bacterial LPS |
| White blood cells (WBCs) | Increasing Concentration of WBCs |
| Procalcitonin (PCT) | Increasing Concentration of PCT |
| Interleukin-6 (IL-6) | Increasing Concentration of IL-6 |
| Interleukin-8 (IL-8) | Increasing Concentration of IL-8 |
| Serum amyloid A (SAA) | Increasing Concentration of SAA |
| Tumor necrosis factor (TNF)-alpha | Increasing Concentration of TNF-alpha |

In some embodiments, devices described herein can also be configured to detect the resolution of an infection. By way of example, when an infection is clearing, various physiological parameters can change in a manner opposite to that described in Table 1 above. As such, in some embodiments, systems and device herein can evaluate physiological parameter measurements to determine if an infection is clearing.

Figure 6:
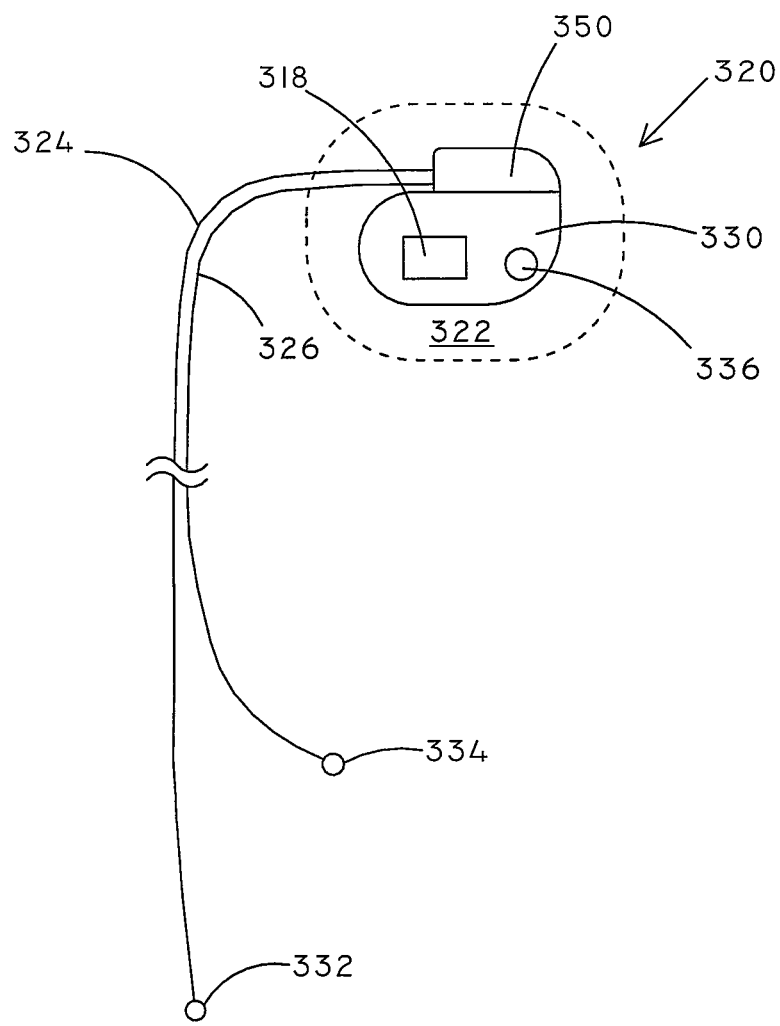
FIG. 6 is a schematic view of an alternative embodiment of an implantable device in accordance with an embodiment of the invention.

Referring now to FIG. 6, another embodiment of a system is shown. The system includes a device 320. The device 320 can include a housing 330 and a header 350. The system can include one or more stimulation leads such as leads 324 and 326 in communication with electrodes 332 and 334 respectively. The system further includes sensor 336. Sensor 336 can generate a signal that can be received and processed by processor 318. In one embodiment, sensor 336 is a temperature sensor. Sensor 336 can be located on the surface of housing 330, within housing 330, outside of housing 330, on the header 350, or within the header 350. Sensor 336 can be used to monitor the temperature of pocket 322 over time. Where the temperature of pocket 322 is found to increase, this may indicate the presence of an infection within pocket 322. In some embodiments, two sensors can be used, one configured to measure temperature within the pocket 322 and another to measure temperature outside of the pocket 322. As such, in some embodiments, changes in local (within pocket) temperature can be distinguished from changes in systemic temperature.

In addition to changes in temperature, it will be appreciated that infections can result in changes to many other physiological parameters. For example, infections can result in the changes indicated in Table 1 above. In some embodiments, sensor 336 can be a chemical species sensor configured to detect various physiological parameters including lactate concentration, pH, C-reactive protein concentration (CRP), lipopolysaccharide concentration, procalcitonin concentration, interleukin-6 concentration, interleukin-8 concentration, serum amyloid A (SAA) concentration, and tumor necrosis factor alpha (TNF-α) concentration. Sensor 336 can also be configured to detect various other physiological parameters including concentrations of potassium ion, sodium ion, calcium ion, glucose, and various blood gases such as $CO_2$. Chemical species sensors of the invention can include, but are not limited to, potentiometric, calorimetric, and fluorimetric sensors. Some exemplary chemical species sensors are described in U.S. patent application Ser. No. 11/383,933, entitled "Implantable Medical Device with Chemical Sensor and Related Methods", the contents of which are herein incorporated by reference. In some embodiments, sensor 336 can be configured to detect physiological parameters including white blood cell counts, and erythrocyte sedimentation rates.

In some embodiments, sensors used for detecting infection can also employ other techniques such as photoplethysmography.

In some embodiments, data provided by a first sensor may be used in conjunction with data provided by one or more other sensors in order to more accurately indicate the presence of an infection. By way of example, excessive pocket fluid accumulation may occur in the absence of infection in a limited number of patients. By analyzing fluid pocket accumulation in conjunction with data from other sensors, it is possible to determine that these particular patients do not have an infection even though they may have pocket fluid accumulation.

In some embodiments, sensor 336 is a pressure sensor. Increased pressure measured by sensor 336 may also be an indication of infection. When tissue becomes infected, the tissue tends to become swollen, and this swelling tends to cause an increase in pressure in the pocket where the device 320 is located.

Figure 7:
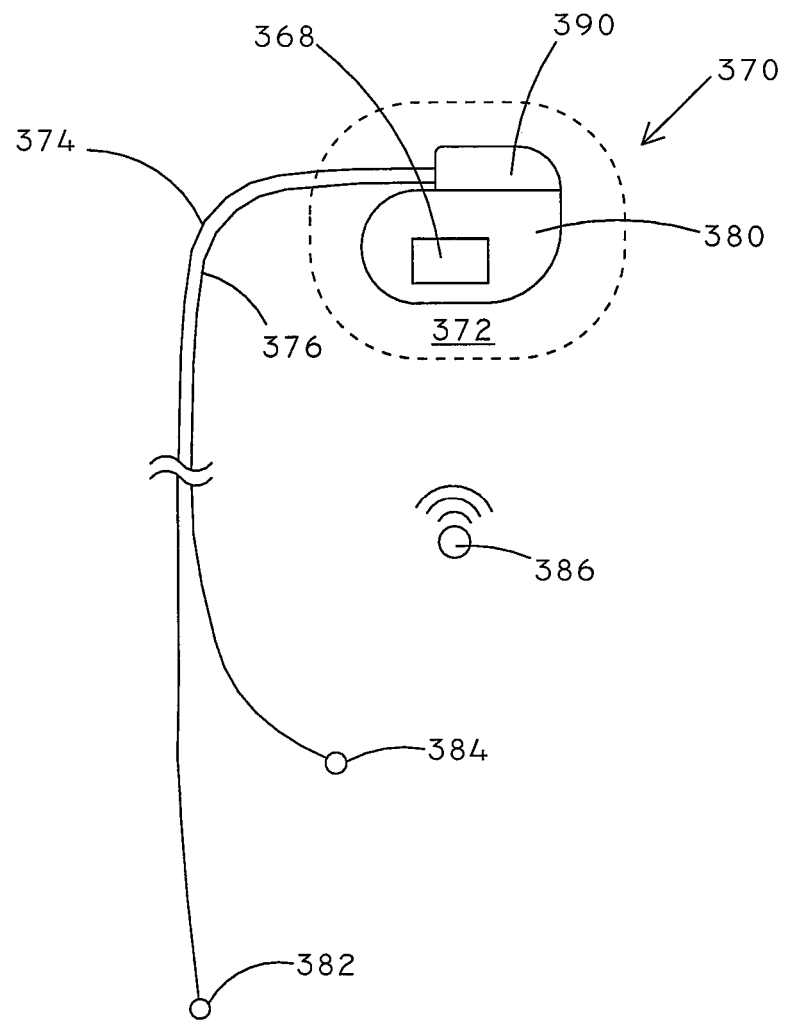
FIG. 7 is a schematic view of an alternative embodiment of an implantable device in accordance with an embodiment of the invention.

It will be appreciated that sensors can be disposed in various places depending on the local tissue to be monitored. By way of example, the sensor can be disposed on or within the pulse generator, on or within the header, on the stimulation leads, remote from the pulse generator, header, or stimulation leads, within the pocket 322, or outside the pocket 322. In some embodiments, sensors can be disposed remotely from other components of the system. By way of example, the sensor can be an untethered or satellite sensor that is in wireless communication with other components of the system. Referring now to FIG. 7, another embodiment of a system for detecting infection is shown. The system includes a device 370 including a housing 380 and a header 390. A controller 368 can be disposed within the housing 380. The system can include one or more stimulation leads such as leads 374 and 376 in communication with electrodes 382 and 384 respectively. The system further includes sensor 386. Sensor 386 can be in wireless communication the controller 368. Sensor 386 can be configured to generate a signal corresponding to a physiological property from which the onset of infection can be detected. In one embodiment, sensor 386 is a temperature sensor. In other embodiments, sensor 386 is an impedance sensor, a pressure sensor, or a chemical species sensor.

Figure 8:
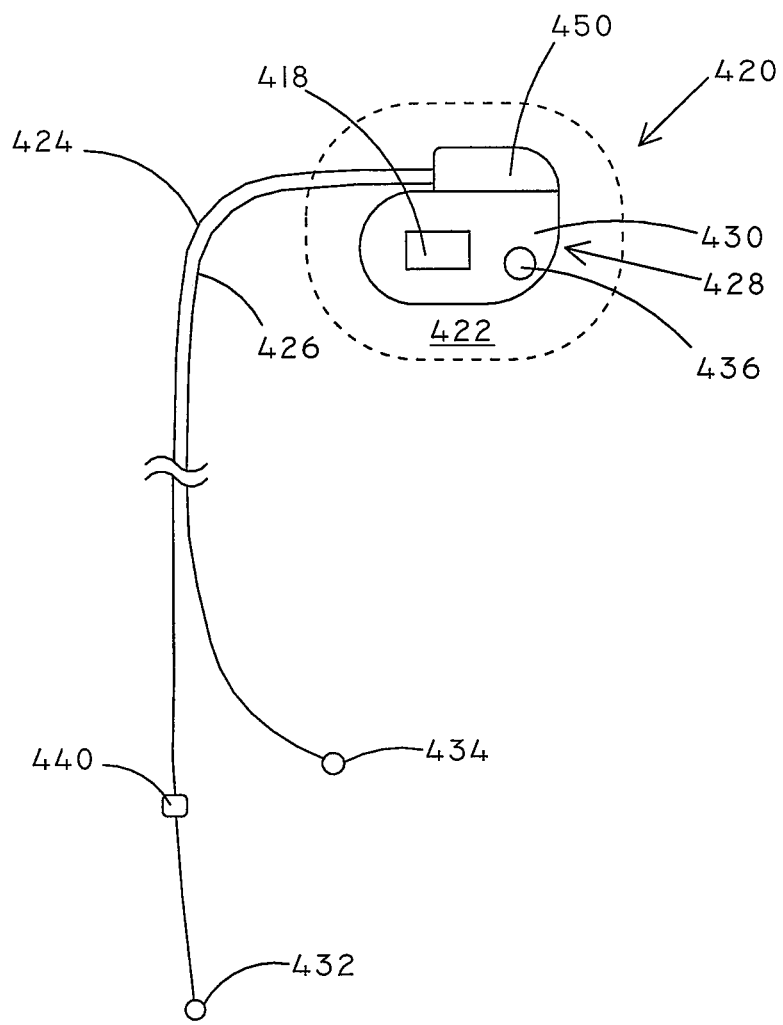
FIG. 8 is a schematic view of an alternative embodiment of an implantable device in accordance with an embodiment of the invention.

In some embodiments, data from sensors measuring conditions within the pocket where the device is implanted can be compared with data from other sensors in the body to determine whether the change was due to changes in the pocket instead of systemic changes. Referring now to FIG. 8, an embodiment is shown including a first sensor 436 and a second sensor 440. In one embodiment, sensor 436 and sensor 440 are temperature sensors. Sensor 436 can be located on the surface of housing 430, within housing 430, outside of housing 430, on the header 450, or within the header 450. Sensor 436 can be used to monitor the temperature of pocket 422 over time. Where the temperature of pocket 422 is found to increase, this may indicate the presence of an infection within pocket 422. Sensor 440 can be used to monitor temperature elsewhere in the body. As such, the signal from sensor 436 can be compared with the signal from sensor 440 in order to determine how the temperature within the pocket is changing relative to how the temperature is changing in other parts of the body.

In some embodiments, the device or system is configured to determine a baseline value or range of values for a physiological parameter over a period of time. This baseline is used to compare to future measurements to determine if an infection has developed. In some embodiments, the comparison or evaluation process to determine if an infection exists is performed by the device or system itself.

Figure 9:
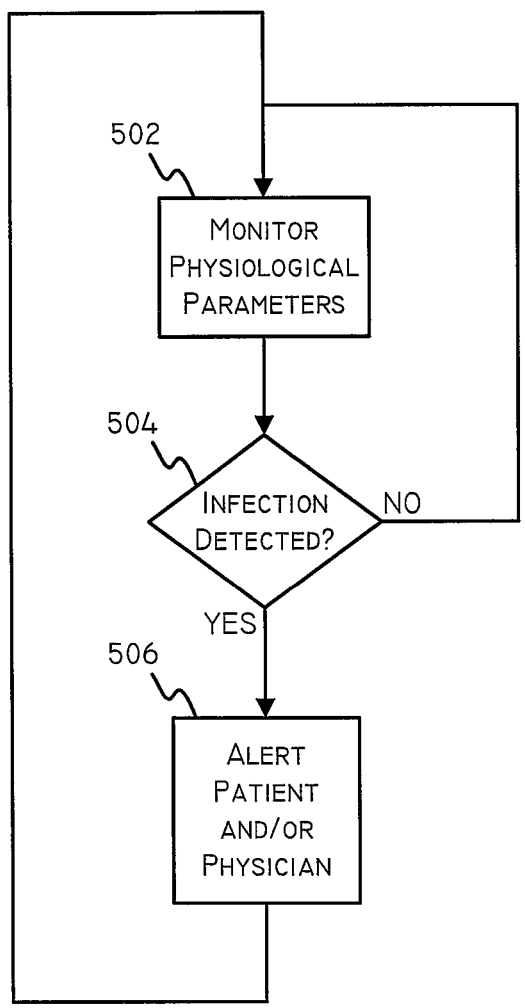
FIG. 9 is an operational flow chart of an implantable device in accordance with an embodiment of the invention.

An embodiment of a method according to the principles of the present invention is depicted in FIG. 9. As shown in step 502, the device monitors physiological parameters using the sensor or sensors previously described. The device further evaluates the physiological parameters as measured in order to determine whether an infection is present at step 504. This can include actions including checking to see if the physiological parameters have exceeded a particular threshold value and checking to see if the physiological parameters follow a trend consistent with the onset of infection. In some embodiments, an infection detection threshold is programmed into the implantable medical device.

In some embodiments, the threshold is a variable parameter that varies with the amount of time lapsed since the device was implanted. For example, because there tends to be a bi-modal distribution of infection rates over time, the threshold may be varied over time to account for this distribution. In specific, a relatively greater number of infections occur either shortly after implantation or during a time window several months after surgery. As such, the threshold can be set to be more sensitive (i.e., a lower threshold) during the periods of higher infection incidence (when the patient is at increased risk of infection), and to be less sensitive (i.e., a higher threshold) during periods of lower infection incidence. This approach helps to minimize false positive tests during low incidence time periods while also helping to ensure that infections are accurately and promptly detected during high incidence periods.

As one example, the threshold can be set lower in the period of time starting shortly after implantation of the device and lasting until approximately four weeks after implantation, and then set higher in the period of time beyond four weeks after implantation. However, it will be appreciated that the time period of four weeks is only one example and that the actual time period used for changing thresholds can depend on various factors. In some embodiments, the time period(s) for changing the threshold can be programmed in by a clinician.

In addition, the threshold can also be set lower (more sensitive) at other times after implantation, such as when the patient is at an increased risk of developing an infection. For example, a lower threshold can be used at any time when the patient undergoes a surgical or dental procedure. As another example, a lower threshold can be used when the patient experiences conditions including, but not limited to, pneumonia, ear infections, eye infections, internal or external ulcerations, skin infections, and the like.

However, it is also known that values of some physiological parameters can vary after implant of a device based on the trauma of the implantation surgery itself and healing processes taking place thereafter. It is not abnormal for some inflammation, tissue heating, and swelling to occur immediately after surgery. These physical changes are similar to the physical symptoms of an infection. Therefore, in order to reduce the incidence of false positives, in some embodiments the system can be configured to wait a brief period of time after surgery to start take measurements and evaluate the presence of an infection. In some embodiments, this period of time can be programmed into the device by a clinician. In some embodiments, this brief period of time can be less than about one week. In other embodiments, the controller can be configured to ignore changes in impedance, temperature, etc. that are below a certain threshold amount during a brief period of time following implantation surgery.

If an infection is detected, then at step 506, the device can be configured to send a notification or warning to the patient. The notification or warning can be auditory, tactile, visual, or the like. The device can also be configured to send a notification or warning to a physician via a patient monitoring system. In one embodiment, a notification may be sent through telemetry.

Figure 10:
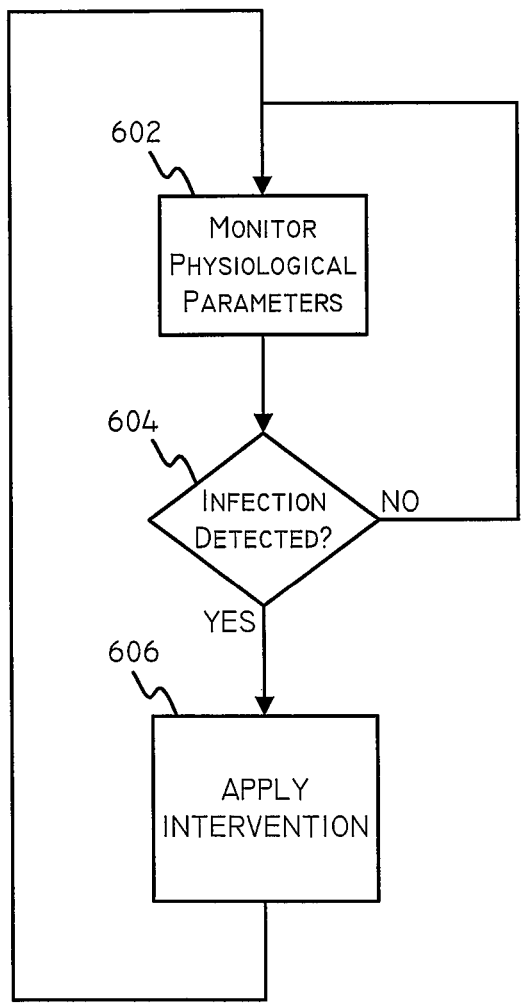
FIG. 10 is an operational flow chart of an implantable device in accordance with an embodiment of the invention.

In some embodiments, a device can be configured to administer therapy in order to treat an infection. Referring now to FIG. 10, an embodiment of a method according to the principles of the present invention is shown. As shown in step 602, the device monitors physiological parameters using the sensor or sensors previously described. The device further evaluates the physiological parameters as measured in order to determine whether an infection is present at step 604. If an infection is detected, then therapeutic intervention can be initiated at step 606. By way of example, initiation of therapeutic intervention can include providing a signal that informs the patient to begin administration of an anti-microbial agent, such as oral antibiotics. As another example, initiation of therapeutic intervention can include releasing an active agent with anti-microbial activity in order to counteract the infection. This step can include activating a drug pump or opening a reservoir in order to release anti-microbial agents such as antibiotics (including vancomycin and gentamicin amongst others), silver ions, and the like. The drug pump or reservoir can be disposed on or in the housing or header, or on the stimulation leads. The drug pump can use various techniques to release the anti-microbial agents including piezo-electric techniques. One example of an implantable drug pump is described in U.S. Pat. No. 7,052,488, the content of which is herein incorporated by reference. In some embodiments, initiation of therapeutic intervention can include initiation of electrical anti-infective therapy. Aspects of electrical anti-infective therapy are described in U.S. Pat. No. 6,282,444, the content of which is herein incorporated by reference.

Figure 11:
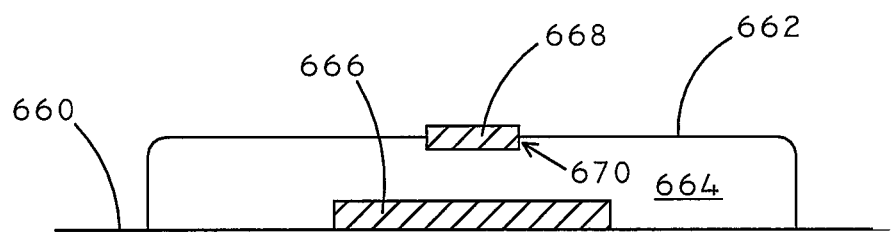
FIG. 11 is a cross-sectional view of a portion of a device in accordance with an embodiment of the invention.

Referring now to FIG. 11, a cross-sectional view of a portion of a device is shown in accordance with an embodiment of the invention. A wall member 662 is coupled to a housing 660, such as the housing of an implanted device. The wall member 662 defines an interior volume, or reservoir 664. An active agent can be disposed within the reservoir 664. For example, an active agent with anti-microbial activity can be disposed within the reservoir 664. A valve member 668 can be disposed over an aperture 670 in the wall member 662. The valve member 668 can selectively open and close to release an active agent disposed within the reservoir 662. An actuator 666 can be disposed within the reservoir 664 in order to facilitate release of the active agent. For example, in an embodiment, the actuator 666 can be a piezo-electric element that selectively increases the pressure within the reservoir 664 causing active agent to be pushed out through the valve member 668.

Systems and methods of the invention can also be used to detect possible outcomes of infection. By way of example, if a local pocket infection spreads, systemic sepsis may result. Systemic sepsis is a life-threatening condition requiring immediate therapeutic intervention. One symptom of systemic sepsis is an elevated respiration rate. In an embodiment, a system can detect a patient's respiration rate in order to detect sepsis. If the patient's respiration rate is found to be greater than 20 breaths per minute, then this can be taken as an indication of sepsis.

Another symptom of systemic sepsis is tachycardia (elevated heart rate). In an embodiment, a system can monitor heart rate in order to detect sepsis. If heart rate is found to be greater than about 90 beats per minute, then this can be taken as an indication of sepsis. In some embodiments, tachycardia indicative of sepsis can include a trend showing an increased heart rate over an individual patient's average heart rate.

Another symptom of systemic sepsis is a body temperature of greater than 100 degrees Fahrenheit or a body temperature of less than 96 degrees Fahrenheit. In an embodiment, a system can monitor temperature in order to detect sepsis. If the body temperature is found to be greater than 100 degrees Fahrenheit or less than 96 degrees Fahrenheit, then this can be taken as an indication of sepsis.

Another symptom of system sepsis is hypocapnia. Hypocapnia is the presence of reduced levels of carbon dioxide in the blood. In an embodiment, a system can monitor the partial pressure of $CO_2$ in the blood ($P_{CO2}$) in order to detect sepsis. Reduced partial pressure of $CO_2$ in the blood can be taken as an indication of sepsis.

Figure 12:
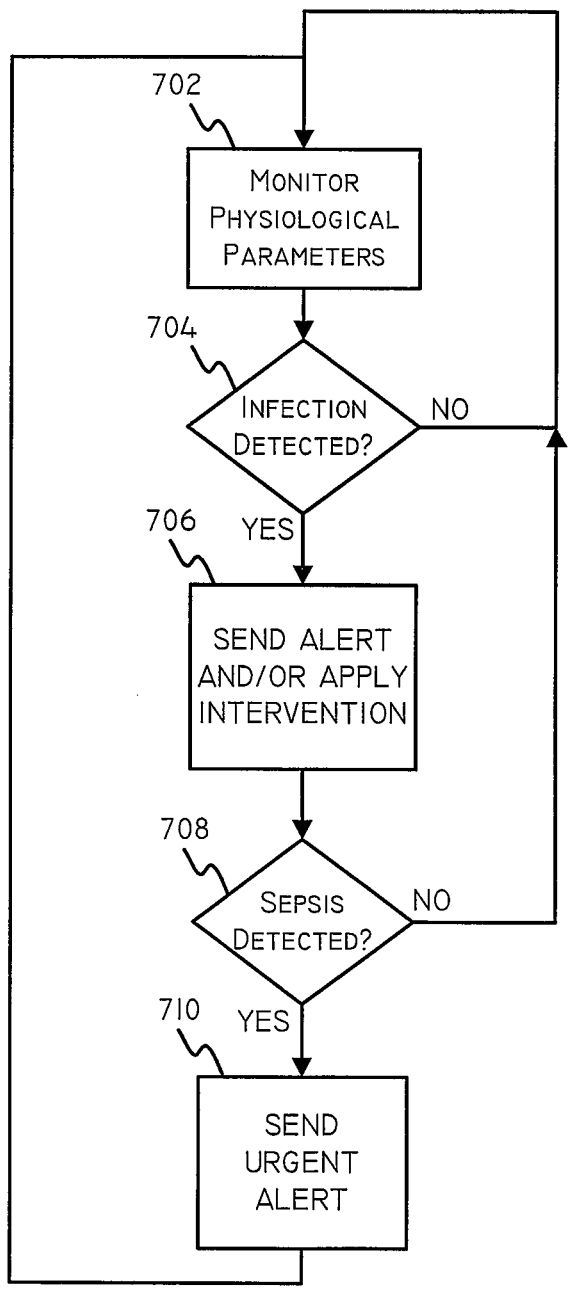
FIG. 12 is an operational flow chart of an implantable device in accordance with an embodiment of the invention.

Referring now to FIG. 12, an embodiment of a method according to the principles of the present invention is shown. As shown in step 702, the device monitors physiological parameters using the sensor or sensors previously described. The device further evaluates the physiological parameters as measured in order to determine whether an infection is present at step 704. If an infection is detected then an alert or notification can be sent and/or therapeutic intervention can be initiated at step 706. Then, at step 708, the system can evaluate whether or not sepsis is occurring according to the techniques described above. If the system determines that one or more indicators of sepsis are present, then the system can send an urgent alert at step 710. This urgent alert can indicate the need to take immediate medical action.

In some embodiments, the implantable medical device can also be configured to monitor the efficacy of an antibiotic treatment regimen initiated after an infection is detected. For example, the implantable medical device may be configured to monitor the same parameters as are used to detect an infection, and to determine from these parameters whether the antibiotic regimen is effective. By way of example, in the context of detecting infection through changes in impedance, a trend showing increased impedance over time after anti-microbial therapy has been initiated can be an indicator that the infection is being effectively treated. In some embodiments, the system can be configured to evaluate whether or not a physiological parameter is indicative of an infection that is being effectively treated and the system can send an alert regarding the same. In some embodiments, there is a separate threshold value for a given physiological parameter that is set to identify when an infection has been effectively treated.

The principles of the invention can be applicable to any implanted device, CRM or otherwise. By way of example, device and methods of the invention can also be applied in the context of implantable neurological stimulation devices. In addition to detection of infection, it will be appreciated that methods and devices of the invention can also be used to detect pocket hematoma, another frequent complication of medical device implants.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A method of detecting infection in a patient comprising:
providing a medical device that is configured to be implanted in a pocket of a patient;
measuring an impedance using a chronically implanted sensor at a plurality of time points, wherein the impedance measurement is taken in the pocket where the medical device is implanted;
measuring the concentration of a chemical species using an implanted chemical sensor;
evaluating the impedance measurement in conjunction with the concentration of the chemical species to determine if infection is indicated, wherein evaluating include comparing the impedance measurement to a detection threshold; and
evaluating additional patient data to detect systemic sepsis including at least one selected from the group consisting of evaluating a respiration rate of the patient to determine if it is greater than 20 breaths per minute and evaluating a heart rate of the patient to determine if it is greater than 90 beats per minute.

2. The method of claim 1, wherein infection is indicated by a decline in an average impedance.

3. The method of claim 1, further comprising initiating therapy to treat infection if infection is indicated.

4. The method of claim 3, the therapy comprising administration of an anti-microbial active agent.

5. The method of claim 3, the therapy comprising initiation of anti-microbial electrical therapy.

6. The method of claim 3, further comprising evaluating the impedance measurements to determine if infection is clearing.

7. The method of claim 1, wherein evaluating the impedance measurements comprises determining a baseline value for the impedance and comparing a current measurement to the baseline value.

8. The method of claim 7, wherein infection is indicated if the current measurement of the impedance differs from the baseline value by at least a threshold amount.

9. The method of claim 1, further comprising providing a notification if infection is indicated.

10. The method of claim 9, wherein providing a notification comprises providing a warning indication to a medical professional via a signal transmitted to a non-implanted device.

11. The method of claim 1, further comprising evaluating the impedance measurements to determine whether or not sepsis is occurring.

12. The method of claim 1, further comprising displaying data regarding the physiological parameter on an external device.

13. The method of claim 1, wherein the chemical species is selected from the group consisting of ionic and non-ionic species.

14. The method of claim 1, wherein the chemical species is selected from the group consisting of hydrogen ion, potassium ion, sodium ion, calcium ion, lactate, glucose, blood gases, and C-reactive protein (CRP).

15. An implantable medical device comprising:
a housing configured to be disposed in a tissue pocket of a patient;
a first electrode disposed on the exterior of the housing configured to provide a first impedance signal;
a second electrode disposed on the exterior of the housing configured to provide a second impedance signal;
a chemical sensor;
a controller disposed within the housing, the controller configured to evaluate the first impedance signal and second impedance signal in conjunction with data from the chemical sensor to determine if an infection is indicated, the controller configured to compare at least one of the first and second impedance signals to a detection threshold;
wherein the first and second impedance signals are reflective of impedance within the tissue pocket of the patient; and
evaluating additional patient data to detect systemic sepsis including at least one selected from the group consisting of evaluating a respiration rate of the patient to determine if it is greater than 20 breaths per minute and evaluating a heart rate of the patient to determine if it is greater than 90 beats per minute.

16. The device of claim 15, wherein the threshold is lower during periods of time when the patient is at increased risk of developing an infection.

17. The device of claim 15, further comprising a reservoir and an anti-microbial active agent disposed within the reservoir, the device configured to release the anti-microbial active agent from the reservoir if an infection is indicated.

18. The device of claim 16, the anti-microbial active agent comprising an antibiotic.

19. The device of claim 16, where the implantable medical device further includes memory configured to store a treatment threshold, where the implantable medical device is configured to compare at least one of the first and second impedance signals to the treatment threshold to determine the efficacy of any medical treatments initiated after an infection is detected.

* * * * *